:::
United States Patent [19]
Clark et al.

[11] Patent Number: 5,095,897
[45] Date of Patent: Mar. 17, 1992

[54] ORTHOPEDIC SPLINT AND METHOD OF CONSTRUCTING SAME

[76] Inventors: E. Nelson Clark, 1941 Lisbon Rd., Chesapeake, Va. 23321; Gretchen Maurer, 1316 Debree Ave., Norfolk, Va. 23517

[21] Appl. No.: 585,980

[22] Filed: Sep. 21, 1990

[51] Int. Cl.$^5$ .................................................. A61F 5/04
[52] U.S. Cl. ...................................... 602/22; 128/880; 2/21
[58] Field of Search ............ 128/77, 87 A, 157, 165, 128/84 R, 880; 2/16, 21, 163, 161 R, 169

[56] References Cited

U.S. PATENT DOCUMENTS

| | | | |
|---|---|---|---|
| 1,268,932 | 6/1918 | Corrigan | 128/84 R |
| 1,641,701 | 9/1927 | Spivak | 2/169 |
| 1,879,609 | 9/1932 | Hannon . | |
| 2,389,237 | 11/1945 | Petrillo | 2/21 |
| 2,552,258 | 5/1951 | Collins | 2/169 |
| 2,688,961 | 9/1954 | Thamas | 128/880 |
| 2,740,121 | 4/1956 | Seidel | 2/21 |
| 3,648,291 | 3/1972 | Pankers | 128/165 |
| 3,872,861 | 3/1975 | Tamny et al. | 128/84 R |
| 3,892,239 | 7/1975 | Masso Remiro | 128/165 |
| 4,084,586 | 4/1978 | Hettrick | 128/157 |
| 4,441,489 | 4/1984 | Evans et al. | 128/77 |
| 4,632,106 | 12/1986 | Gamm | 128/165 |
| 4,644,941 | 2/1987 | Ogle, II | 128/87 |
| 4,694,843 | 9/1987 | Casenhiser | 2/21 |
| 4,832,010 | 5/1989 | Lerman | 128/165 |
| 4,899,737 | 2/1990 | Lazarian | 128/87 A |

FOREIGN PATENT DOCUMENTS

| | | | |
|---|---|---|---|
| 217451 | 4/1987 | European Pat. Off. | 128/77 |
| 80145 | 5/1918 | Switzerland | 128/157 |
| 727324 | 3/1955 | United Kingdom | 128/165 |

OTHER PUBLICATIONS

Bauer & Black, *Surgery, Gynecology & Obstetrics*, vol. 96, No. 2, Feb. 1953, p. 63.
A Handbook of Experiences With the Application of Wrist, Hand and Finger of those, by Donald J. McDougall, David A. Carus & Amar S. Jain, undated.
North Coast Medical, Inc. Hand Therapy Catalog, 1990.
Hand Splinting Principles and Methods, by Elaine Ewing Fess, M.S., O.T.R., Karen S. Gettle, O.T.R., James W. Strickland, M.D., 1981.
Rehabilitation of the Hand, by James M. Hunter, M.D., Lawrence H. Schneider, M.D., Evelyn J. Mackin, L.P.T., Anne D. Callahan, M.S., O.T.R., 1984.

*Primary Examiner*—Richard J. Apley
*Assistant Examiner*—Linda C. M. Dvorak
*Attorney, Agent, or Firm*—Griffin, Branigan & Butler

[57] ABSTRACT

An orthopedic splint (10) comprises a neoprene rubber tube having an internal surface forming a curved splint passage (50) for snugly fitting on a joint (14, 16) to be treated and defining a radially directed internal ridge (52) extending lengthwise along the tube for pressing against the joint. The splint is constructed by folding in half a flat sheet of neoprene rubber (18), attaching free end portions (26, 28) of the sheet to form a transition tube (44) having a transition internal passasge (46), sewing a seam (40) in said free adjacent free edge portions to define a wedge shaped angle pointing away from the transition internal passage having an angle of between 140°–160°, cutting away excess neoprene sheet so as to leave a V-shaped seam allowance (42) at the free edge portions beyond the seam to form the ridge, and turning the transition tube inside out to form the splint (10).

27 Claims, 2 Drawing Sheets

ORTHOPEDIC SPLINT AND METHOD OF CONSTRUCTING SAME

BACKGROUND OF THE INVENTION

This invention relates to dynamic orthopedic splints and, in particular, to such splints used to correct joint angulation deformities of distal and proximal interphalangeal joints, respectively known as DIP and PIP joints.

Muscles and tendons at finger joints often produce a state of chronic, or residual, flexion contraction in which they prevent fingers and joints thereof from being completely straightened. This, temporarily reduces joint mobility of patients' fingers and if it is maintained for long periods of time can cause permanent loss of mobility. Such loss of finger joint mobility is often treated by application of an orthopedic splint to a stricken finger to slowly elongate muscle and tendon tissue thereof, thereby reversing contraction without causing damage, such as tearing of tissue. Such a splint, while progressively stretching appropriate tissue, should also maintain a range of motion for joints being treated. Therefore, it is an object of this invention to provide an orthopedic splint which progressively straightens a joint while allowing the joint a range of motion.

One manner of treating chronically contracted fingers involves use of a splint having a metallic spring contacting the treated finger at three pressure points. One pressure point is at or near a back (dorsal) surface of a joint while the other two pressure points are on under (volar) surfaces adjacent and on opposite sides of the joint. Such an arrangement is disclosed in HAND SPLINTING PRINCIPLES AND METHODS by Elaine Ewing Fess, et al, published by The C. V. Mosby Company in 1981. A similar orthopedic splint is disclosed in U.S. Pat. No. 4,441,489 to Evans et al which discloses a spring attached to a finger at various pressure points on opposite sides of a finger joint which applies pressure for straightening a joint.

Although these pressure-point splints have been effective in treating joint contractures, they do have disadvantages. For one thing, they are relatively difficult and expensive to construct, often involving pluralities of parts which must be intricately attached together. For this reason, it is an object of this invention to provide an orthopedic splint which is uncomplicated to construct and which can therefore be relatively inexpensively constructed.

When a joint is being treated as described above, it is important to maintain heat on the joint because heat increases flexibility of tissue and also promotes healing. Most prior art orthopedic splints do not provide adequate heat to joints. Therefore, it is another object of this invention to provide an orthopedic splint which automatically retains body heat about joints being treated.

Yet another difficulty with many prior-art finger splints is that they are cumbersome and obstructive so that it is difficult for patients, when wearing them, to use their digits. In this regard, it is quite helpful if patients can continually use their fingers, while wearing such splints so that treated joints thereof do not become stiff. Therefore, it is an object of this invention to provide an orthopedic splint which allows a limb on which the splint is mounted to be continually used.

It is important when treating a residual flexion contracture of a joint to prevent swelling of the joint because such swelling can also cause stiffness of the joint and inhibit healing. Therefore, it is another object of this invention to provide an orthopedic splint which prevents swelling of a joint being treated therewith.

Yet another difficulty with many prior-art orthopedic splints is that their individual springs must be carefully matched with different size and shaped joints. It is often time-consuming to fashion an orthopedic splint to a particular joint with these prior-art systems. Thus, it is an object of this invention to provide an orthopedic joint which can be quickly and easily customized to a joint to be treated.

Another difficulty with some prior art orthopedic splints is that because they are uncomfortable due to points of pressure, and/or cumbersome, patients cannot wear them for long periods of time, thereby decreasing their effectiveness. Therefore, it is still another objection of this invention to provide an orthopedic splint which is not unduly uncomfortable and/or inconvenient for a patient and therefore can be worn for long periods of time.

Another problem with some prior art splints is that because of their intricacies, they must be carefully handled when not mounted on a joint. For example, it is not advisable to carry some such splints in pockets or purses because the splints may be thereby damaged. Further, such splints when thusly stored may be cumbersome for users because of their rigidity. For this reason, it is another object of this invention to provide an orthopedic splint which can be easily carried by a user in a pocket, purse, or the like.

A NeoSleeve TM neoprene rubber sleeve is advertised on page 69 of a 1990 North Coast Medical, Inc. catalog which is an approximately 1/16 inch thick tube formed from neoprene rubber into which a finger is to be inserted for warming arthrictic digits. Such a sleeve is not particularly effective for straightening joints. Therefore, it is an object of this invention to provide an orthopedic splint, and a method of making the same, which not only keeps digits warm but also effectively straightens them.

SUMMARY OF THE INVENTION

According to principles of this invention, an orthopedic splint comprises a curved tube of flexible material having an internal surface forming a curved splint passage of an approximate longitudinal shape toward which a joint to be treated is biased and having a cross-sectional size and shape such that the internal surface fits snugly on the joint to be treated with the internal surface defining a radially-directed internal ridge extending lengthwise along the tube for pressing against the underside of the joint. The orthopedic splint is constructed by folding a sheet of flexible material on itself, cutting a V-shape at adjacent free ends of the sheet, preparing a seam along the adjacent free ends leaving a seam allowance to form the ridge, and turning the transition tube inside out so that the ridge is on the internal surface of the tube forming the splint passage. The tube thickness in a preferred embodiment is between 1/16 inch and ¼ inch, preferrably around ⅛ inch.

BRIEF DESCRIPTION OF THE DRAWINGS

The foregoing and other objects, features and advantages of the invention will be apparent from the following more particular description of a preferred embodiment of the invention, as illustrated in the accompanying drawings in which reference characters refer to the same parts throughout the different views. The drawings are not necessarily to scale, emphasis instead being placed upon illustrating principles of the invention in a clear manner.

DESCRIPTION OF A PREFERRED EMBODIMENT

Figure 1:
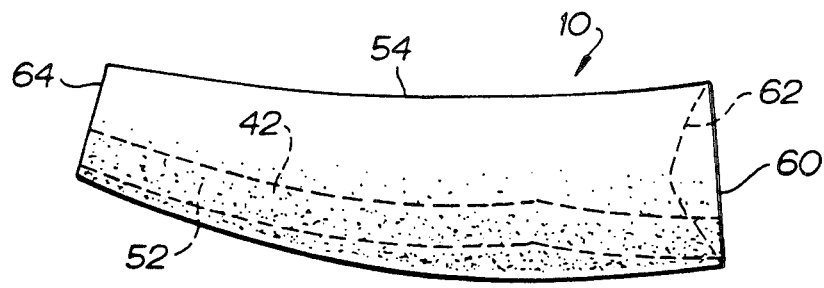
FIG. 1 is a side elevational of an orthopedic splint according to principles of this invention.
Figure 2:
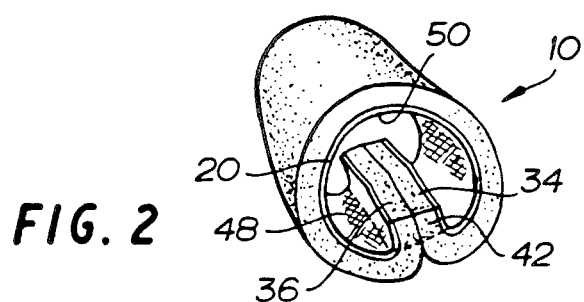
FIG. 2 is an end view of the orthopedic splint of FIG. 1.
Figure 3:
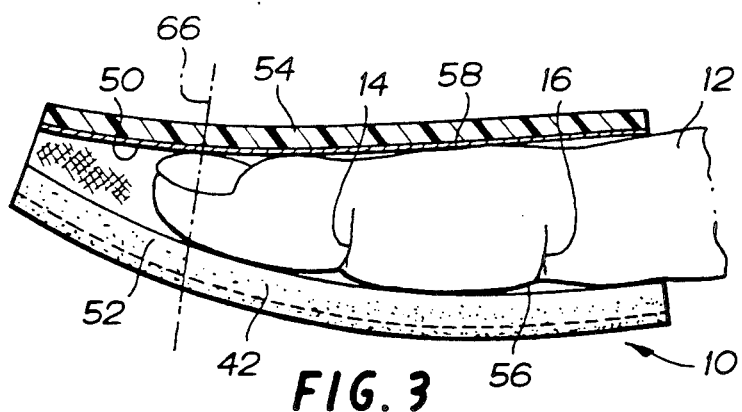
FIG. 3 is a side cross-sectional view of the orthopedic splint of FIGS. 1 and 2 with a straight finger therein.
Figure 3A:
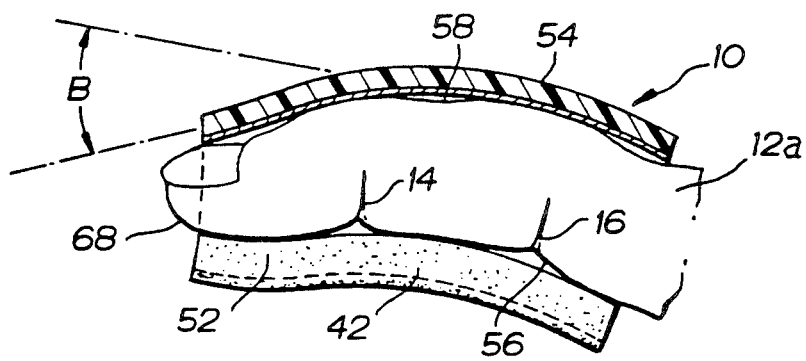
FIG. 3A is a side cross-sectional view of the orthopedic splint of FIGS. 1 and 2 with a finger having an angulation deformity therein.
Figure 4:
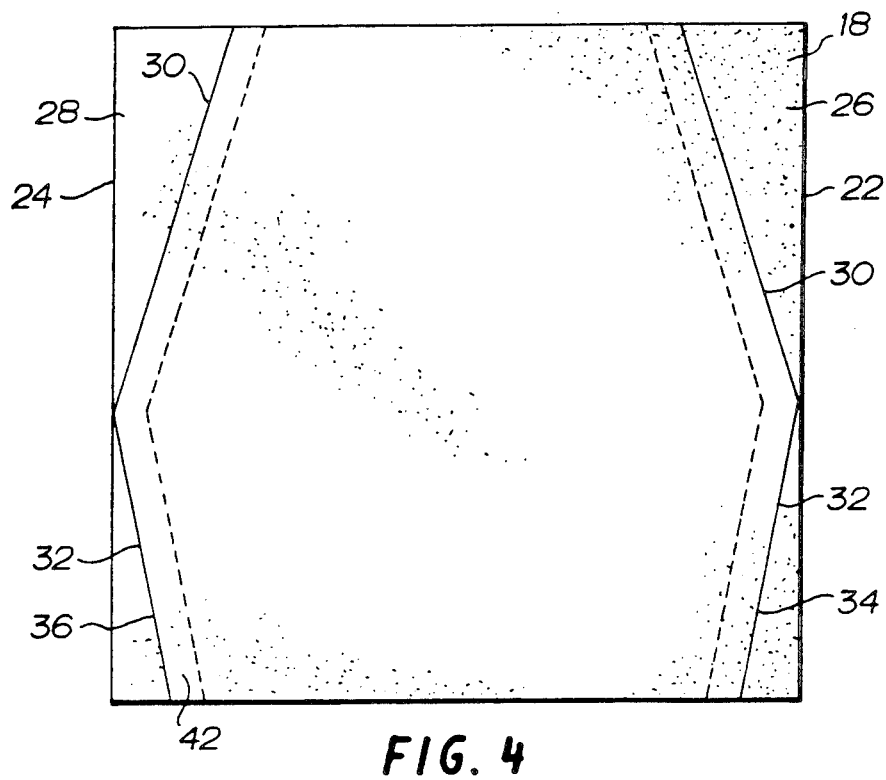
FIG. 4 is a plan view of a sheet of neoprene rubber used in making the splint of FIGS. 1 and 2 with seam and cut lines indicated thereon in dashed lines.
Figure 5:
FIG. 5 is an elevational end view of the sheet of neoprene rubber of FIG. 5 with cut lines being shown thereon with dash lines.
Figure 6:
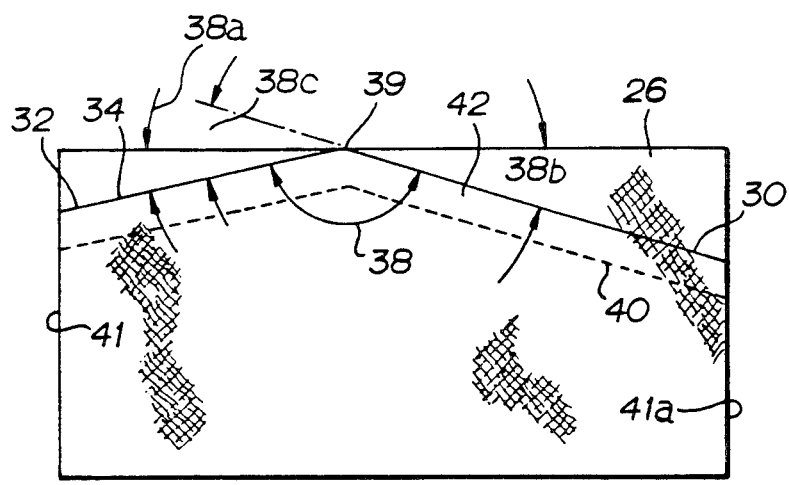
FIG. 6 is a side elevational view of a transition tube constructed with the sheet of neoprene rubber of FIGS. 4 and 5 during a step of construction.
Figure 7:
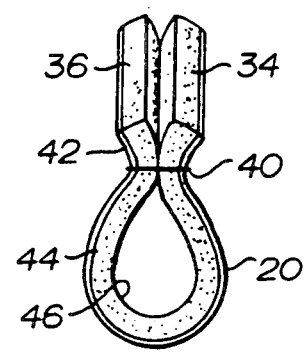
FIG. 7 is an end view of the transition tube of FIG. 6.

A curved orthopedic splint 10 to be used for treating fingers 12 and 12a having a distal interphalangeal joint (DIP joint) 14 and a proximal interphalangeal joint (PIP joint) 16 is depicted in FIGS. 1-3. In this regard, either the DIP joint 14 or the PIP joint 16, or both, has a residual flexion contracture, which means that it is chronically bent, as depicted in FIG. 3A, and that a patient to whom the finger 12a belongs cannot straighten the joint. Usually, such a condition is only treated if the joint cannot be rotated closer than 20° to straight, that is, if PIP joint 16 is chronically bent more than an angle B of 20° from a straight line, such as 25°-35°, it is treated.

A method of constructing the orthopedic splint 10 is depicted in FIGS. 4-7. First, a flat sheet 18 of approximately ⅛" neoprene rubber having approximate dimensions of 4"×4", lined with cloth 20 on one side, is folded on itself so that free ends 22 and 24 are adjacent one another with free-end portions 26 and 28 lying flat against one another with the cloth lining being on the outside. The free-end portions 26 and 28 are simultaneously cut along lines 30 and 32 so as to create wedge, or V-shaped free edges 34 and 36. In this regard, an angle 38 of the V-shape is between 140°-160° and preferably is around 150°, with the angles 38a and 38b being 15° each. That is, this angle 38 causes the V-shaped free edges 34 and 36 to deviate from a straight line an angle 38c by between 20° and 40°, preferably around 30°. An apex point 39 of the V-shaped free edges is spaced 2" inches from a first end edge 41 and 2" inches from a second end edge 41a. Thus, in one embodiment the V-shape is relatively symmetrical, although this is not necessary. A seam 40 is then stitched along the V-shaped free edges 34 and 36 leaving a seam allowance 42 of approximately ⅛ inch between the V-shaped free edges 34 and 36 and the seam 40. This creates a transition tube 44 having a transition internal passage 46. In this respect, the transition passage 46 is designed to snugly fit the finger 12a to be treated. The transition tube 44 is then turned inside out to form the curved orthopedic splint 10 of FIGS. 1-3A. The cloth lining 20 now forms a surface 48 of a splint internal passage 50. The seam allowance is radially directed into said splint internal passage 50.

The curved orthopedic splint 10 is used by sliding it onto the finger 12a with a ridge 52 formed by the seam allowance 42 being positioned on the volar (bottom or underside) surface of the finger 12. As can be seen in FIG. 1, when the finger 12 is not in the orthopedic splint 10 the orthopedic splint 10 has a curved banana shape, with a dorsal wall 54 being slightly bowed upwardly at ends thereof, and with the internal ridge 52 extending upwardly, partially collapsing the splint internal passage 50. The orthopedic splint, in some cases, is curved beyond a desired shape of a finger. That is, the curve can be opposite to a direction in which a joint is naturally bent so as to bias the joint toward a shape which is beyond its natural straight shape. When the orthopedic splint 10 is placed on the finger 12a the internal ridge 52 presses upwardly against a volar surface 56 of the finger 12a and a dorsal surface 58 of the finger 12a is urged against the bowed dorsal wall 54. The combined pressure of the internal ridge 52 and the bowed dorsal wall 54 tend to rotate the DIP joint 14 and PIP joint 16 to straightened attitudes as represented by the finger 12.

In a preferred embodiment, the seam allowance 42 is approximately ⅛" wide.

It should be understood that the seam could be formed by heat, or other, bonding, in which case, it is possible to bond the entire width of the seam allowance together.

One can trim the proximal end 60 of the orthopedic splint 10, along dash line 62 in FIG. 1 for example, to fashion the orthopedic splint for fitting around digit web spaces of a hand. A distal end portion 64 of the orthopedic splint 10 can be cut away, for example along dashed line 66 in FIG. 3, so that a distal end 68 of the finger 12 is exposed for use by the patient as depicted in FIG. 3A.

From tests conducted to date, it appears that the sleeve must be manufactured from a piece of neoprene rubber or other similar flexible material which is greater than 1/16 inch thick in order for it to be effective but that it cannot have a thickness greater than ¼ inch. In this regard, if the material is as thin as 1/16 inch it does not appear to have sufficient strength to properly pressure a joint toward a desired configuration. If it is greater than ¼ inch thick it is too bulky and has too much strength to apply proper pressure and to allow proper movement. It appears that a proper thickness is around ⅛ inch.

It will be understood by those of ordinary skill in the art that the orthopedic splint of this invention acts against a bent, or contracted finger 12a in a gentle fashion in order to return the DIP and PIP joints 14 and 16 to more normal straightened positions of a finger 12.

Further, the orthopedic splint of this invention, being constructed of a solid sheet of neoprene rubber, serves to maintain heat around the finger, or digit, 12a, thereby assisting in relaxing tendinous structures in the finger 12a, and promoting healing.

Still further, the orthopedic splint provides compression along the entire finger to aid in reduction of edema (swelling). Reduction of swelling promotes healing and also maintains mobility of the DIP and PIP joints 14 and 16.

In addition, the orthopedic splint 10 is flexible so that a patient can continue to use his finger 12 while he is wearing the orthopedic splint 10. Not only is use of the finger 12 helpful to the patient, but it also aids in healing by not allowing the DIP and PIP joints 14 and 16 to become stiff and/or frozen.

It should also be appreciated that an important benefit of this invention is that the orthopedic splint 10 can be easily and conveniently carried in a pocket or purse without damage to the orthopedic splint 10.

This invention employs elastic properties of neoprene rubber, or some other flexible material, to allow joint mobility while at the same time using a specially constructed seam to stretch and correct deformities. The invention allows joint mobility during rehabilitation and helps dissipate edema and harmful fluids that lead to scar tissue.

While the invention has been particularly shown and described with reference to a preferred embodiment, it will be understood by those skilled in the art that various changes in form and detail may be made therein without departing from the spirit and scope of the invention. For example, although the invention is described as being made with a neoprene sheet having a cloth lining, the cloth lining is not necessary for proper operation of the orthopedic splint, but rather provides comfort to a patient and is helpful in sliding the splint on a joint. Along these lines, it would also be possible to have a cloth lining on both sides of the neoprene sheet, however, this would create a cloth lining on the outer surface of the orthopedic splint which would decrease friction thereat making it more difficult for a patient to use the splint for manipulating papers and the like.

Although the splint is described for use on finger joints, it would also be possible to use the splint on knee, elbow, wrist, ankle, and other joints.

In constructing the orthopedic splint 10, one could either sew the seam 40 before trimming along cut lines 30 and 32, or one could first trim along the cut lines 30 and 32 before sewing or otherwise attaching the seam 40.

It may also be possible to construct a bowed or banana shaped splint sleeve in another way than that described herein.

Further, the seam need not be sewn, but could be created by some other type bonding, such as adhesive, heat, or solvent bonding.

The embodiments of the invention in which an exclusive property or privilege are claimed or defined as follows:

1. An orthopedic finger splint for treating finger joint angulation deformities comprising a tube of flexible material with a thickness greater than 1/16 inch, said tube having a dorsal side for contacting a dorsal surface of the finger joint and a volar side for contacting a volar surface of the finger joint, said tube defining an internal surface forming a splint passage with an approximate longitudinal shape toward which a finger joint to be treated is to be biased, said splint passage having a cross-sectional size and shape such that said internal surface of said splint passage fits snugly on the finger joint when the finger joint is placed therein, said internal surface defining a radially-directed internal ridge extending lengthwise along the volar side of the tube, opposite the dorsal side, for pressing against a volar surface of the finger joint when the finger joint is placed in said passage.

2. An orthopedic finger splint as in claim 1 wherein said splint is constructed by the method steps of:
    folding a substantially flat sheet of flexible material in half with free edge portions being flat against one another to form a transition tube having a transition internal passage to approximately snugly fit the joint to be treated;
    attaching said free edge portions together to form a seam having a seam allowance;
    turning said transition tube inside out so as to form a splint tube having a splint internal passage with said seam allowance forming said radially directed internal ridge therealong.

3. An orthopedic finger splint as in claim 2 wherein said step of attaching said free edge portions together is accomplished by sewing.

4. An orthopedic finger splint as in claim 2 wherein is further included in said method of constructing said orthopedic splint the step of cutting free edge portions to define a V-shaped angle of between 140° and 160°.

5. An orthopedic finger splint as in claim 4 wherein said angle of said V-shaped cut is approximately 150°.

6. An orthopedic finger splint as in claim 4 wherein said V-shape of said V-shaped free edges is a symmetrical V.

7. An orthopedic finger splint as in claim 2 wherein said flexible material is a neoprene rubber.

8. An orthopedic finger splint as in claim 2 wherein said splint passage is curved along a length thereof.

9. An orthopedic finger splint as in claim 8 wherein said internal ridge is directed radially in a direction toward which ends of said splint passage are curved.

10. An orthopedic finger splint as in claim 1 wherein the flexible material has a thickness less than ¼ inch.

11. An orthopedic finger splint as in claim 10 wherein the flexible material thickness is approximately ⅛ inch.

12. A method of constructing an orthopedic splint for treating joint angulation deformities comprising the steps of:
    folding a substantially flat sheet of flexible material in half with free edge portions being flat against one another to form a transition tube having a transition internal passage to approximately snugly fit said joint to be treated;
    forming said free edge portions to define a V-shaped angle of between 140° and 160°;
    attaching said free edge portions together to form a seam having a seam allowance;
    turning said transition tube inside out so as to form a splint tube having a splint internal passage with said seam allowance forming a radially directed internal ridge therealong.

13. A method as in claim 12 wherein said step of attaching said free edge portions together is accomplished by sewing.

14. A method as in claim 12 wherein is further included in said method of constructing said orthopedic splint using neoprene rubber as the material.

15. A method as in claim 12 wherein said angle of said V-shaped cut is approximately 150°.

16. A method as in claim 12 wherein said V-shape of said V-shaped free edges is approximately a symmetrical V.

17. A method as in claim 12 wherein the sheet of flexible material has a thickness greater than 1/16 inch and less than ¼ inch.

18. A method as in claim 17 wherein the thickness is approximately ⅛ inch.

19. A method as in claim 12 wherein said seam is fabricated to be approximately ¼ inch wide.

20. An orthopedic finger splint for treating finger joint angulation deformities comprising a tube of flexible material having a dorsal side for contacting a dorsal surface of the finger joint and volar side for contacting a volar surface of the finger joint, said tube defining an internal surface forming a gradually-curved splint passage with an approximate longitudinal shape toward which a finger joint to be treated is to be biased, said splint passage having a cross-sectional size and shape such that said internal surface of said splint passage fits snugly on the finger joint when the joint is placed therein, ends of said dorsal side being curved away from said volar side wherein said gradual curve is in an opposite direction than a finger joint to be treated with said splint normally bends during manipulation thereof.

21. An orthopedic finger splint as in claim 19 wherein said tube of flexible material has a thickness greater than 1/16 inch but less than ¼ inch.

22. An orthopedic finger splint as in claim 21 wherein said thickness is approximately ⅛ inch.

23. An orthopedic finger splint as in claim 20 wherein said gradual curve resemble the curve of a banana.

24. An orthopedic finger splint as in claim 20 wherein said orthopedic finger splint has a longitudinal ridge in said splint passage for pressing against a volar surface of the finger joint.

25. An orthopedic finger splint as in claim 24 wherein said longitudinal ridge extends along the entire length of said orthopedic finger brace.

26. An orthopedic finger splint for treating finger joint angulation deformities comprising a tube of flexible material having an internal surface forming a splint passage with an approximate longitudinal shape toward which a joint to be treated is to be biased, said splint passage having a cross-sectional size and shape such that said internal surface of said splint passage fits snugly on the joint when the joint is placed therein, and said tube of flexible material having a thickness greater than 1/16 inch but less than ¼ inch.

27. An orthopedic finger splint as in claim 26 wherein said thickness is approximately ⅛ inch.

* * * * *